United States Patent [19]

Weitl et al.

[11] 4,442,305

[45] Apr. 10, 1984

[54] POLYCATECHOLAMIDE CHELATING AGENTS

[75] Inventors: Frederick L. Weitl, Martinez; Kenneth N. Raymond, Berkeley, both of Calif.

[73] Assignee: The United States of America as represented by the United States Department of Energy, Washington, D.C.

[21] Appl. No.: 295,512

[22] Filed: Aug. 24, 1981

[51] Int. Cl.$^3$ .............................................. C07C 101/72
[52] U.S. Cl. .................................... 562/451; 564/154; 564/157; 564/158; 424/308; 424/309; 424/324
[58] Field of Search ....................... 424/308, 309, 324; 564/158; 562/451

[56] References Cited

U.S. PATENT DOCUMENTS 3,022,268  2/1962  Armitage ............................. 564/158
3,869,443  3/1975  Lesher ................................. 564/158
4,181,654  1/1980  Weitl ............................ 260/239 BC

FOREIGN PATENT DOCUMENTS 1529150  10/1978  United Kingdom ......... 260/259 BC

OTHER PUBLICATIONS

J. L. Corbin et al., Biochemistry 8, 757–762, (1969).

G. H. Tait, Biochem. J. 146, 191, (1975).

Primary Examiner—Paul J. Killos
Attorney, Agent, or Firm—Harold M. Dixon; Roger S. Gaither

[57] ABSTRACT

Novel polybenzamide compounds useful for in vitro or in vivo chelation are described. The compounds have the formula

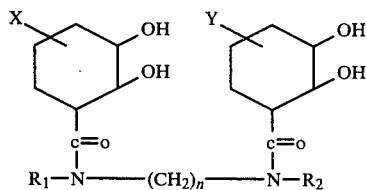

Polyamines are reacted with 2,3-dimethoxy benzoyl chloride unsubstituted or substituted with $SO_3H$, $SO_3M$, $NO_2$, $CO_2H$ or $CO_2M$ as desired is reacted with a polyamine in an inert solvent then demethylated with $BBr_3$ or $BCl_3$ in an inert solvent. Where compounds symmetrically substituted on the terminal N's are desired, the polyamine is first reductively alkylated by reaction with an aldehyde or ketone and the resulting Schiff base is hydrogenated.

14 Claims, No Drawings

POLYCATECHOLAMIDE CHELATING AGENTS

BACKGROUND OF THE INVENTION

The invention described herein was made at Lawrence Berkeley Laboratory in the course of or under U.S. Department of Energy Contract No. W-7405-ENG-48 with the University of California.

The present invention relates to the preparation of novel polybenzamide compounds which have several uses. More particularly, this invention relates to the preparation of novel poly (2,3-dihydroxybenzoic acid) amides, compounds which can be varied substantially in molecular weight and N-terminal substitution to provide variations in physical properties such as water and oil solubility to enhance their effect in in vitro and in vivo applications.

Plutonium and other actinides present special problems to animals and their complete removal or elimination in a non-toxic or other non-hazardous way is highly desirable. Removal of actinides by a ligand or chemotherapeutic agent within an acceptable range of biological half-life of the agent is also desirable. In addition, the removal and recovery of actinides from liquids such as radioactive wastes is of great technological importance. Selectivity in both in vivo and in vitro applications is extremely important and desirable.

As pointed out in our recent U.S. Pat. No. 4,181,654 chemotherapeutic attempts to remove ingested heavy metals and particularly plutonium from the tissues of animals have followed along traditional application of such chelating agents as ethylenediaminetetraacetic acid. The results have not been very encouraging since such ligands also complex the trace metal ions essential to the organism and are not extremely strong sequestering agents for the actinides.

Chelating agents for the actinides, as mentioned, also have important technological applications. Such agents are useful in the separation of actinide elements, particularly from radioactive wastes generated by fission power reactors. Plutonium is recovered and purified on a commercial scale by extraction in liquid-liquid systems at normal temperature, using organic complexing agents as extractants.

It is known that the 2,3-dihydroxybenzoic (DHB) acid amides of glycine, serine, lysine, threonine, and spermidine are naturally occurring compounds for sequestering Fe(III). (References: J. Ito and J. B. Neilands, *J. Am. Chem. Soc.* 80, 4645–4647, 1958; J. L. Corbin and W. A. Bulen, *Biochemistry* 8, 757–762, 1969; H. Korth, *Arch. Mikrobiol.* 70, 297, 1970; and G. H. Tait, *Biochem. J.* 146, 191, 1975). N(DHB)glycine and N(DHB) lysine have been chemically synthesized by the condensation of the O-protected amino acids with DHB acid, mediated by N,N'-dicyclohexylcarbodiimide (see Ito et al, op. cit., and Corbin et al, op. cit.)

Compounds into which a radionuclide can be incorporated, which are non-toxic or relatively so and with an acceptable biological half-life have beneficial effects on animals with respect to various diagnostics, conditions, diseases and maladies (i.e. radiopharmaceuticals) are also important and are desirable.

OBJECTS OF THE INVENTION

It is a principal object of this invention to provide novel poly (2,3-dihydroxybenzoic acid) amines having several important uses.

It is another object of this invention to provide novel compounds having an adjustable biological half-life, and adjustable, selective, or otherwise improved chelating properties for in virto and/or in vivo applications.

Still another object is to provide intermediates for pharmaceutically active compounds with a low order of toxicity.

Yet another object is to provide a process for producing novel poly benzamides wherein the benzoyl moiety more specifically contains catecholate hydroxyl substituents and with or without additional aromatic substituents.

An additional object of this invention is to provide compounds which are intermediates to compounds having a radio-nuclide therein, and/or variable biological half-life, capable of bioconcentration and having anti-carcinogenic activity.

Other objects and advantages of the present invention will become apparent from the description herein taken as a whole.

SUMMARY OF THE INVENTION

The present invention provides novel compounds of the formula:

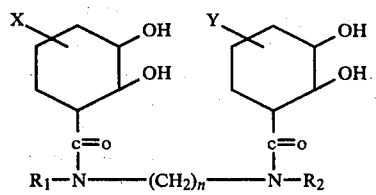

in which:

n is an integer varying from about 1–8, inclusively;

X and Y are independently selected from the group consisting of H, $SO_3H$, $SO_3M$, $NO_2$, $CO_2H$ and $CO_2M$;

where M represents a metal selected from the group consisting of alkali metals and alkaline earth metals, $R_1$ is selected from the group consisting of H, hydrocarbon radicals and the benzamide moiety

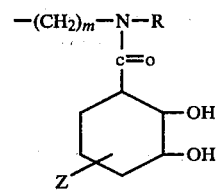

where m is an integer varying from 1–8, inclusively and can be the same or different than n;

Z is selected from the same group as X and Y;

R is selected from the same group as $R_1$, and when the R's (i.e. R, $R_1$ and $R_2$) are other than H, they can be joined to form a cyclic azaalkane;

$R_2$ is selected from the group consisting of hydrocarbon radicals and the benzamide moiety described above;

with the provisos that:

when $R_1$ is hydrogen then $R_2$ must be at least one said benzamide moiety; and, when $R_1$ is a hydrocarbon radical $R_2$ must be the same hydrocarbon radical (i.e. the molecule must be symmetrical); and, when the molecule contains less than five benzamide moieties at least one of X, Y and Z must be a $CO_2H$ or $CO_2M$ substituent.

Preferably X, Y and Z are $CO_2H$ or $CO_2M$ even when the number of benzamide groups is 5 or more.

The above compounds are prepared by: reacting a polyalkylene amine with a preformed 2,3-dimethoxybenzoyl chloride or 2,3-dioxomethylenebenzoyl chloride in the presence of at least one reaction mediator (i.e. an acid acceptor and a weak acid or base) at a temperature in the range of about room temperature to over 100° C. to form the corresponding benzamide intermediate compound, then demethylating the intermediate by treatment with boron tribromide ($BBr_3$) or boron trichloride ($BCl_3$) in a dipolar, aprotic (i.e. an inert) solvent at a temperature in the range of about $-20°$ C. (i.e. minus 20° C.) to 50° C.

Where one or more of the R's represents a hydrocarbon radical such as incorporated into the molecule by reductive alkylation using a ketone or aldehyde corresponding to the hydrocarbon radicals to be attached to the terminal nitrogens. The reaction with the aldehyde or ketone is in water, alcohol or aqueous alcohol medium with a hydrogenation catalyst and a hydrogen rich atmosphere at pressures of about atmospheric to several atmospheres at about 20°-50° C.

More particularly R, $R_1$, and $R_2$ can be hydrocarbons selected from alkyls, (straight chain, branched and cycloalkyls) and aralkyls as follows:

alkyls of about 1-20 carbon atoms, preferably 1-10 carbon atoms with 3-10 carbon atoms being more preferred, aralkyls can be about 1-20 carbon atoms, preferably 1-10 carbon atoms with 3-10 being more preferred. The aralkyl radicals can be made of alternating arylene and alkylene radicals having an alkylene structure or moiety in a terminal position with the dangling valence therefrom for attachment to a nitrogen in the molecule.

Alkyl radicals are generally preferred for the R's as defined above over the other radicals described above.

Examples of the radicals contemplated are:
alkyls methyl, ethyl, propyl, isopropyl, cyclopentyl, pentyl, neopentyl, hexyl, cyclohexyl, nonyl, decyl, dodecyl, tetradecyl, and eicosyl;

aralkyls benzyl, phenethyl, phenyl propyl, bibenzyl, phenylbutyl, phenylhexyl, phenyldodecyl, tetradecylphenyl, bibenzyl, and biphenyl, naphthyl, anthracyl, or terphenyl attached through an alkylene such as methylene.

More particularly n and m can independently represent an integer selected in the range of about 1-10; preferably they represent an integer in the range of 3-6 but more preferably 4. Examples of the alkylene groups represented by $-(CH_2)n$ or m—are methylene, ethylene, propylene, isopropylene, butylene, hexylene and decylene. Higher alkylene groups can be used but the reaction rates in their preparation are generally unacceptably slow.

Examples of the alkali and alkaline earth metals represented by M are sodium, potassium, lithium, calcium, magnesium, barium, radium and zinc.

As those skilled in the art can readily appreciate where $R_1$ and/or $R_2$ represents

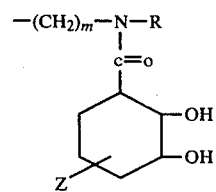

the R's ($R_1$, $R_2$ and R) can cumulatively represent a molecule having a plurality of N-substituted benzamide moieties of at least three (but when the total is less than five, at least one of X, Y and Z is a $CO_2H$ or $CO_2M$ radical). Thus it is apparent that polymeric forms of the compounds are included in this invention, that is compounds of the formula

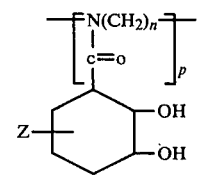

where p is an integer of at least 3. For example polyethyleneimines of 14, 28 and 42 nitrogens are commercially available and can be used as the starting amine to be reacted with the benzoyl chloride moiety to form the corresponding polybenzamide compound. That is, compounds with 14, 28, 42 and higher numbers of benzamide moieties with polyethyleneimine molecular weights of about 1000 or 2000 and higher and in turn polybenzamide molecular weights of about 3000 and higher are included in this invention. Compounds having molecular weights above about 40,000 are not ordinarily prepared because of difficulties in doing so and particularly because of long reaction times due to "steric hindrance". The higher molecular weight compounds are water-insoluble however the polymers will still be water soluble at high pH's on the order of 12 and above. The water solubility versus oil solubility characteristic also applies to the compounds wherein the terminal R's are hydrocarbon radicals. Typically the compounds shift from water solubility to oil solubility where the R's are alkyls of at least about 10 carbon atoms (e.g. bis-decyl compounds) or aralkyls of at least about 7 carbon atoms (e.g. bis-benzyl compounds).

The preferred compounds are those where X, Y and Z represent $X—CO_2H$, that is the 2,3-dihydroxyterephthalate derivatives for certain applications. Still more preferred, particularly for in vivo application are said terephthalate derivatives where the R's are hydrocarbon radicals or the polymeric forms discussed above. Polymers appropriate for drug use must be water soluble at physiological pH's i.e. pH $\sim$7.4 and small enough in molecular weight to be excreted from the body either in feces or urine or subject to degradation within the host to make excretion possible.

The selective, reductive alkylation briefly described above can be carried out as a single step or as a two step process. In the latter case the reaction of the aldehyde or ketone to first form a Schiff base, is achieved by reaction of the aldehyde or ketone with the polyamine in water, alcohol or an aqueous alcohol solution at a temperature of about room temperature (i.g. 20°-25° C.) to 50° C., and then the Schiff base is hydrogenated in a second step. Severe hydrogenation conditions should be avoided to prevent side reactions such as reduction of the aldehyde or ketone. Room temperature is generally preferred for the first step. An example of hydrogenation catalysts which can be used is 5% palladium on carbon. Hydrogen pressures can vary but can be as low as about 1 atmosphere (approx. 15 psi) to as high as about 4 atmospheres (approx. 60 psi) in appropriate pressure equipment. Pressures of about 15 to 45 psi will generally be preferred as in a Paar shaker. The reaction was carried out until no further hydrogen uptake was observed.

The alkylated amine prepared according to the above procedure is next reacted with the appropriate benzoyl chloride moiety containing compound. For example 2,3-dimethoxyterephthaloyl chloride (or the corresponding 2,3-dioxo compound) at a temperature of about room temperature to over 100° C. Preferably this reaction is carried out at about 20° to 60° C. The amide formation requires the use of at least one reaction mediator as a solvent. For example, N,N-dimethylacetamide (DMAA), or tetrahydrofuran (THF) and dimethylformamide (DMF) which function to provide a dipolar, aprotic solvent. Also making up the solvent system is at lest one acid acceptor such as pyridine; 4-N,N-dimethylaminopyridine, triethylamine (TEA or NEt$_3$).

The poly (2,3-dimethoxyterephthalamide) product can be demethylated by reaction with BBr$_3$ or BCl$_3$ at −20° C. (i.e. minus 20° C.) to 50° C., but preferably at about room temperature (i.e. 20°–25° C.) to 35° C. The reaction medium for this deprotection or de-methylation is an inert or substantially inert solvent, including for example, the halogenated compounds such as methylene chloride, chloroform, dichloroethane, and carbon tetrachloride.

Introduction of additional aromatic substituents on the benzoyl (or terephthaloyl) moiety of the molecule (e.g. SO$_3$H) is preferably carried out as a final reaction step after the demethylation using the procedures outlined in our U.S. Pat. No. 4,181,654.

In order to disclose more clearly the nature of the present invention and the advantages thereof, reference will hereinafter be made to certain specific embodiments which illustrate the herein-described invention. It should be clearly understood, however, that this is done solely by way of example and is not to be construed as a limitation upon the spirit and scope of the appended claims.

DETAILED DESCRIPTION OF PREFERRED EMBODIMENT

Reductive Alkylation

Melting points were taken on a Buchi apparatus in open capillaries and are uncorrected. H$^1$NMR spectra were recorded on a Varian A-60 instrument using Me$_4$Si (non-aqueous) or 3-Me$_3$-Si-1-propane sulfonic acid, sodium salt, hydrate (D$_2$O) as internal standard. Infrared spectra were recorded on a Perkin-Elmer 283 instrument. Evaporations were accomplished in vacuo with a Buchi Rotovapor-RE at 55°. Column chromatography was performed with 60–200 mesh silica gel in a 35×2.5 cm o.d. column. Microanalyses and EI-mass spectra (m/e, 70 eV) were performed by Analytical Services, Chemistry Department, University of California, Berkeley. Spermidine (1) and spermine (2) were purchased from Ames Laboratories, Inc., Milford, Conn. Except for tetrahydrofuran (THF) which was purified by distillation from CaH$_2$ and 2,3-dimethoxybenzoyl chloride (DMBCl) which was prepared immediately before use from the acid (Aldrich Chem. Co., Milwaukee), all chemicals were used without further purification.

EXAMPLE 1

1, 10-Bisisopropyl-1,5,10-triazadecane, trihydrochloride (1a).

The following reactants were weighed into a Paar shaker bottle (500 mL) and hydrogenated at 1–3 atm., 20°–5°, for 48 hours: spermidine (5.0 g, 34.5 mmol), H$_2$O (25 mL), (CH$_3$)$_2$CO(25 mL), 5% Pd/C (0.5 g, cat.). The product mixture was filtered to remove catalyst, then conc. HCl added to achieve pH 1. Evaporation gave a solid which was dissolved in hot CH$_3$OH. Subsequently, addition of an equal volume of EtOH with ice cooling and scratching provided fine white crystals of 1a (9.3 g, 80%, air dried at 110°): mp 263°–5°, HNMR (D$_2$O)δ1.32 (d, 12H, J$_{AB}$=6.5 Hz, (CH$_3$)$_2$CH—), 1.5–2.5 (broad, m, 6H, —NH$_2$CH$_2$CH$_2$—), 2.9–3.6 (broad m, 10H, CH—NH$_2$—CH$_2$—). Anal. Calcd for C$_{13}$H$_{31}$N$_3$ 3HCl: C, 46.09; H, 10.12, N, 12.40; Cl, 31.39. Found: C, 45.95; H, 10.04; N, 12.29; Cl, 31.42.

EXAMPLE 2

1,10-Bis-n-decyl-1,5,10-triazadecane, trihydrochloride (1b)

To an EtOH (95%, 50 mL) solution of spermidine (7.3 g, 50 mmol) immersed in a water bath (20°–5°) was added dropwise, with stirring, n-decyl aldehyde (17.2 g, 110 mmol). The reaction solution was stored under argon overnight before 5% Pd/C (1 g, cat.) was added as an aqueous slurry. Hydrogenation (72 hrs) and recrystallization from hot, acidic, aq. EtOH gave (1b) (9.2 g, 34%): mp 292°–5°d; HNMR (TFA) 0.8–2.3 (complex m, 44H,$_+$—CH$_2$(CH$_2$)$_8$CH$_3$ and —NH$_2$—CH$_2$CH$_2$—), 3.0–4.0 (broad m, 12H, —NH$_2$CH$_2$—), 7.0–8.7 (broad m, 6H, —NH$_2$—). Anal. Calcd for C$_{27}$H$_{59}$N$_3$.3HCl; C, 60.60; H, 11.68; N, 7.85; Cl, 19.87. Found: C, 60.97; H, 11.62; N, 7.63; Cl, 19.62.

EXAMPLES 3–7

| Example No. | Procedure | Amine | Reaction Time | Alkylating Agent |
| --- | --- | --- | --- | --- |
| 3. | Example 2 | spermidine | 1 hr. | benzaldehyde |
| 4. | Example 1 | spermidine | 72 hrs. | cyclohexanone |
| 5. | Example 1 | spermine | 48 hrs. | acetone |
| 6. | Example 2 | spermine | 95 hrs. | n-decylaldehyde |
| 7. | Example 2 | spermine | 72 hrs. | cyclohexanone |

Amide Formation

EXAMPLE 8

N$^{1,10}$-Bisisopropyl-N$^{1,5,10}$-Tris-(2,3-dihydroxybenzoyl)-1,5,10-triazadecane (3a)

To 2,3-dimethoxybenzoyl chloride (DMBCl, 45 mmol) dissolved in tetrahydrofuran (THF, 100 ml) was added 1a (5.1 g, 15 mmol). To this vigorously stirred slurry was added NEt$_3$ (12.5 ml, 90 mmol) via pipette, resulting in substantial heat evolution. After stirring overnight in a 60° oil bath, by-product NEt$_3$HCl was removed by filtration and washed with THF. The combined filtrate was evaporated to crude product, further purified by chromatography on silica gel using 0-4% (v/v) EtOH in CHCl$_3$ solutions. Thus was obtained the yellow oil-glass permethyl-intermediate (8.5 g, 79%) satisfactory for use in the synthesis of 3a. Note: ir (neat, KBr) showed the complete absence of any peak in the 3400-3200 cm$^{-1}$ (—CONH—) region. Also the HNMR (CCl$_4$) 0.9-1.4 (br m, 12H, (CH$_3$)$_2$CH—) indicated magnetically inequivalent isopropyl groups (normally expected to give a sharp doublet with $J_{AB}=7$ Hz, as in 1a). De-O-methylation of the permethyl intermediate (8.5 g, 12 mmol) in CCl$_4$ (50 mL) solution was achieved (under argon) by dropwise addition to a vigorously stirred solution of BBr$_3$ (9 ml, 890 mmol) in CH$_2$Cl$_2$ (200 mL). The reaction vessel was immersed in a room temperature water bath and allowed to stir overnight before workup. Next the dropwise addition of H$_2$O (50 mL) (caution, HBr gas) served to hydrolyse the borates; the resulting aqueous HBr was neutralized to pH 4 by addition of 6 N aq. NaOH. Solid product was isolated by filtration, dissolved in alcohol, and precipitated by dropwise addition to vigorously agitated H$_2$O (5 volumes). Filtration, water wash, and vacuum drying over P$_2$O$_5$/NaOH pellets at room temperature gave amorphous 3a (7.0 g, 88%) 135°-45°; HNMR(TFA) 1.2-1.7 (br m, 12H, (CH$_3$)$_2$CH—), 1.5-2.7 (br m, 6H, NCH$_2$CH$_2$—), 3.3-4.6 (br m, 10H, CHNCH$_2$—), 6.9-7.5 (br m, 15H, ArH(OH); ir (KBr) 3600-3100 (OH), 1605,1580 (—CONR—), 1470, 1360, 1280, 790, 747 cm$^{-1}$, m/e (rel. int.), 637 (M, 0.5), 501 [M—C$_6$H$_3$(OH)-CO$_2$, 5], 402(3), 365(M-[C$_6$H$_3$(OH)CO$_2$]$_2$,41), 195 (71), 154(93), 136 (C$_6$H$_3$(OH)CO$_2$, 100).

Anal. Calcd for C$_{34}$H$_{43}$N$_3$O$_9$ 2.5H$_2$O: C, 59.81; H, 7.09; N, 6.15. Found: C, 59.56; H, 7.45; N, 6.18.

EXAMPLE 9

N$^{1,10}$-Bisdecyl-N$^{1,5,10}$Tris(2,3-dihydroxybenzoyl)-1,5,10-tri-azadecane (3b)

Using the same procedure as for 3a the following reactants were combined: DMBCl (30 mmol), 1b (5.4 g, 10 mmol), THF (75 ml), NEt$_3$ (8.3 mL, 60 mmol). Purification as before provided oil-glass permethyl precursor (7.3 g, 79%) satisfactory for use in the final step: m/e (rel. inten.), 917(M,6), 886(M—OCH$_3$,28), 776 [M—(CH$_2$)$_9$CH$_3$,13], 752 [M—C$_6$H$_3$(OCH$_3$)$_2$CO, 33], 165 [C$_6$H$_3$(OCH$_3$)$_2$CO, 40]. As before, BBr$_3$ (6 mL, 60 mmol) in CH$_2$Cl$_2$ (150 mL) solution and permethyl precursor (7 g, 7.7 mmol) in CCl$_4$ (75 mL) solution were combined. Following reaction, H$_2$O (75 mL) followed by 6 N aq. NaOH added to achieve pH 4 water layer. Separation of the organic layer followed by several water washes, MgSO$_4$ drying, and filtration gave a light yellow product solution. This was concentrated then added dropwise to a large volume of vigorously stirred (60°-90°) petroleum ether. The resulting precipitate was collected by filtration, redissolved in EtOH and evaporated to dryness. Vacuum drying (50°, overnight) gave amorphous 3b (5.6 g, 88%): mp 63°-65°; HNMR (CDCl$_3$) δ0.8-1.4 (br m, 34H, —N(CH$_2$)(CH$_2$)$_7$CH$_3$), 1.2-0.2 (br m, 10H, —NCH$_2$CH$_2$—), 2.9-3.9 (br m, 12H, —NCH$_2$—), 6.5-7.0 (br m, 9H, ArH), 7.7-8.4 (br, 6H, ArOH); ir (KBr) 3600-3100 (OH), 2930 (—CH—), 2860 (—CH—), 1610, 1585 (—CONR), 1466, 1280, 1070, 790, 750 cm$^{-1}$; m/e (rel. inten.) 833 (M,4), 697 [M—C$_6$H$_3$OH)CO$_2$, 20], 136[C$_6$H$_3$(OH)CO$_2$, 100]. Anal. Calcd for C$_{48}$H$_{71}$N$_3$O$_9$—C, 69.12; H, 8.58; N, 5.04. Found: C, 68.72: H, 8.72; N, 4.95.

EXAMPLES 10-12

| Example No. | Procedure | Amine Source | Catechol Benzoyl Chloride |
| --- | --- | --- | --- |
| 10 | Example 8 | Example 3 | DMB Cl |
| 11 | Example 8 | Example 4 | DMB Cl |
| 12 | Example 8 | Example 5 | DMB Cl |

PREPARATION STARTING WITH CATECHOL

General Procedure

To achieve good water solubility in the catecholate ligands via the carboxylate moiety, the symmetrical 2,3-dihydroxyterephthalic acid was used. Thus the dry disodium salt of catechol was carboxylated according to a modified procedure of Cason and Dyke (J. Am. Chem. Soc. 1950, 72, 621). The dry disodium carboxylate derivative provided crystalline dimethyl ester upon refluxing with HCl/CH$_3$OH. Permethylation to a tetramethylated ligand was achieved with K$_2$CO$_3$/dimethyl sulfate in refluxing acetone. When a hot CH$_3$OH solution of the ligand 2,3-dimethoxy-1,4-dimethylterephthate was treated with 1 equiv. of 6 N NaOH overnight, a 70% yield of the monosodium salt resulted. Neat SOCl$_2$ at 50° C. converted this compound directly to acid chloride, the necessary synthon for preparation of permethyl tetraamide and permethyl triamide. Demethylation with excess BBr$_3$ at room temperature provided the spermine and spermidine derivatives. Both were purified by acid-base precipitation and were dried over P$_2$O$_5$ under vacuum.

Melting points were taken on a Buchi apparatus in open capillaries and are uncorrected. Infrared spectra were recorded on a Perkin-Elmer 283 instrument. Proton NMR spectra were recorded on a Varian A-60 instrument using Me$_4$-Si-1-propane sulfonic acid, sodium salt, hydrate as internal standard. Evaporations were accomplished under vacuum (oil pump) with a Buchi Rotovapor-RE at ≦55° C. Thin layer chromatography (TLC) was performed on precoated 60F —254 silica gel sheets, developed in tetrahydrofuran/C$_6$H$_{12}$/H$_2$O (93:7:5) and visualized with UV, I$_2$ vapor, or Fe$^{+3}$/H$_2$O/EtOH spray. Column chromatography was performed using 60-200 mesh silica gel in a 35×2.5 cm o.d. column and fractions monitored by TLC. Microanalyses and mass spectra (m/e, 70 eV) were performed by Analytical Services, Chemistry Department, University of California, Berkeley. Both spermine and spermidine were purchased from the Ames Laboratories, Inc., Milford, Conn. The BBr$_3$ used was a product of Alfa Division, Ventron Corporation, Danvers, Mass. All chemical analyses were within 0.4% of calculated values. Those elements analyzed appear after each empirical formula.

EXAMPLE 13

Disodium 2,3-dihydroxyterephthalate

The procedure of Cason and Dyke has been modified as follows: To catechol, (33 g, 300 mmol) dissolved in 300 ml CH$_3$OH (under argon atmosphere) was added at once NaOH pellets (24 g, 600 mmol). The resulting solution was allowed to sit overnight then evaporated in vacuo (105°, 48 hr) to a light tan, dry powder which was further treated with excess CO$_2$ (1100 psi) at 175°-200° (48 hr) in a static, stainless steel bomb. The light tan solid product was acidified with hot aq. 6 N HCl, filtered, and washed with hot H₂O. The solid product was dissolved in hot aqueous NaOH, (pH 9), treated twice with charcoal, then cooled in an ice bath to obtain nearly white, crystalline disodium 2,3-dihydroxyterephthalate (17.6 g, 24%): mp>300°; ¹HNMR (D₂O) δ7.45 (s, 2H, Ar$\underline{H}$). The remaining (basic solution was acidified with aq. HCl, to obtain additional nearly white product (20.8 g, 35%).

mp 289°–90°; ¹HNMR (DMSO) δ7.42 (s, 2H Ar$\underline{H}$). Anal. (C₈H₄O₆Na₂) Na.

EXAMPLE 14

Dimethyl-1,3-dihydroxyterephthalate

To a slurry of the above disodium salt (12.1 g, 58 mmol) in 150 ml CH₃OH was added excess HCl via gas diffusion tube. After 60 hr under reflux, the hot reaction mixture was filtered to remove NaCl. Ice bath cooling provided white needles of the dimethylester the salt (20.7 g, 82%): mp 141°–3°; ¹HNMR (DMSO) δ4.13 (s, 6H, —CO₂C$\underline{H}$₃), 7.36 (s, 2H, Ar$\underline{H}$).

EXAMPLE 15

Dimethyl-2,3-dimethoxyterephthalate

The following materials were combined and kept at reflux (under argon) 48 hr: the above dimethyl ester (13.6 g, 60 mmol), K₂CO₃ (16.6 g, 120 mmol), dimethyl sulfate (11.4 ml, 120 mmol), acetone (150 ml). Filtration while hot to remove salts, followed by distillation in vacuo gave corresponding dimethyl ester-dimethoxy (10.3 g, 68%): b₀.₅ 130°; n$_D$ 1.5156; ¹HNMR (CCl₄) δ3.8–4.0 (two s, 12H, OCH₃+CO₂CH₃), 7.49 (s, 2H, Ar$\underline{H}$).

EXAMPLE 16

Sodium Methyl 2,3-dimethoxyterephthalate

To the above dimethyl ester-dimethoxy product (10.1 g, 40 mmol) in CH₃OH (200 ml) solution was added NaOH (1.6 g, 40 mmol) and H₂O (5 ml). The resulting solution was refluxed overnight, then concentrated in vacuo to about ¼ volume. Addition of acetone (several volumes) to precipitate a small amount of disodium by-product followed by filtration gave a clear colorless solution. Addition of ethyl ether corresponding monosodium, monomethyl ester-dimethoxy product (1–2 vol) with scratching gave white microcrystalline (7.1 g, 68%) which was dried at 75° (<1 mm): mp 205°–7°; ¹HNMR (D₂O) δ3.9–4.0 (two s, 9H, OCH₃+CO₂CH₃), 7.30 (d, 1H, J$_{AB}$=9 Hz, Ar$\underline{H}$), 7.70 (d, 1H, J$_{AB}$=9 Hz, Ar$\underline{H}$).

Anal. (C₁₁H₁₁O₆Na) Ch, H, No.

EXAMPLE 17

Methyl-2,3-dimethoxyterephthaloyl chloride

The above monosodium (6.5 g, 25 mmol) was added in portions to SOCl₂ (25 ml) with the evolution of SO₂ and heat. After stirring overnight under a Drierite tube an equal volume of CCl₄ was added and the mixture filtered to remove NaCl. Coevaporation of this solution in vacuo with CCl₄ (3×30 ml) gave white, crystalline CCl₄-soluble acid chloride (~100%), which was satisfactory for immediate use in the synthesis of the amide intermediate.

EXAMPLE 18

N,N',N'',N'''-Tetra(2,3-dimethoxy-4-carbomethoxybenzoyl-1,5,10,14-tetraazatetradecane To the crude, dry acid chloride product above (25 mmol) was added tetra-hydrofuran (THF (50 ml), spermine (1.2 g, 6.0 mmol), and NEt₃ (3.5 ml, 25 mmol). An immediate white precipitate formed and the evolution of heat was evident. The reaction was allowed to stir overnight at ambient temperature in a stoppered flask. Filtration, THF wash, then oven drying provided NEt₃.HCl (3.2 g, 97%). Evaporation of the THF solution in vacuo gave a viscous oil; this was dissolved in a small amount of CHCl₃, then eluted from a silica gel column (initially with CHCl₃). The product was eluted with 2–4% CH₃OH in CHCl₃ (v/v): TLC, R$_f$ 0.63. Coevaporation (in vacuo) with CCl₄ (3×50 ml) gave a glassy solid which when dried at 56°, 5 microns, 20 hr gave the desired final product identified above ⅜ ccl₄ (6.2 g, 86%): ir (neat, NaCl) 3380 (—CON$\underline{H}$—), 2940 (—CH—), 1730 (—$\underline{C}$O₂CH₃), 1665–1625 (—$\underline{C}$ONR—), 1520, 1455, 1400, 1305–1235, 1020, 755 cm⁻¹; ¹HNMR (CCl₄) δ1.2–2.2 (broad m, 8H, NCH₂C$\underline{H}$₂), 3.0–4.1 (broad m, 12H, NC$\underline{H}$₂CH₂), 2.8–4.2 (broad s, 36H, —OC$\underline{H}$₃+—CO₂C$\underline{H}$₃), 6.8–7.9 (broad m, 8H, Ar$\underline{H}$).

Anal. (C₅₄H₆₆N₄O₂₀.⅜CCl₄) C, H, N.

CHELATION

In Vivo

The compounds of this invention may be used to remove various metals from mammals including humans by various modes of administration such as injection of aqueous solutions intravenously (I.V.), injection intramuscularly (I.M.) injection intraperitoneally (I.P.), or ingestion orally. The tables below show data on various prior art compounds and compounds according to the present invention. Although the tables do not make such apparent, the compounds containing a carboxyl aromatic substitutent (e.g. a terephthaloyl moiety) are significantly less toxic than the sulfonated compounds. The higher molecular weight and more lipophilic compounds also were more effective in removing metals such as plutonium from the liver. The compounds of this invention were tested on mice in obtaining the data in the tables. They have also been successfully tested on dogs with low toxicity based on gross histological examination. Also it is to be understood that while only Pu(IV) chelation is shown by the tables below, different species of these compounds can be used to chelate other metal ions in the +4 or (IV) state such as actinides (IV) Th (IV) and U (IV), Ga(+3), Fe(+3), In(+3), etc.

In Vitro

In vitro chelation can be carried out at a wide range of pHs (e.g. 5–11). This method requires only the physical admixing to form a liquid-liquid system at room temperature and atmospheric pressure to achieve a measure of chelation.

Effect of catechoylamide sulfonates and carboxylates and related compounds on retention of ²³⁸Pu(IV) in the mouse. [a,b]

TABLE I

| | IUPAC NAME BELOW | $^{238}$Pu excreted (% of dose) |
|---|---|---|
| Sulfonated compounds | | |
| 3,4,3-LICAMS | (1.) | 65 |
| 3,3,3,3-CYCAMS | (2.) | 35 |
| Carboxyl compounds | | |
| 3,4,3-LICAMC | (3.) | 69 |
| 3,3,3,3-CYCAMC | (4.) | 59 |
| Poly-LICAMC | (5.) | 37 |
| DHTA[b] | (6.) | 9.7 |
| DHPA[b] | (7.) | 9.0 |
| DHIPA[b] | (8.) | 5.3 | footnotes to Table 1

[a]Ligands were administered (i.p.) 1 hr and mice were killed 24 hr after injection (i.v.) of $^{238}$Pu citrate.
[b]Ligand dosage was 30μ mole/kg except for the monomers, DHTA, DHPA, and DHIPA, for which the dosage was 480μ and DHBA, for which the dosage was 78μ mole/kg.
(1.) $N^1,N^5,N^{10},N^{14}$—tetra(2,3-dihydroxy-5-sulfobenzoyl-tetraazatetradecane
(2.) $N^1,N^5,N^9,N^{13}$—tetra(2,3-dihydroxy-5 sulfobenzoyl)tetraazacyclohexadecane
(3.) $N^1,N^5,N^{20},N^{24}$—tetra(2,3-dihydroxy-4-carboxy-benzoyl)-tetraazatetradecane
(4.) $N^2,N^5,N^9,N^{23}$—tetra(2,3-dihydroxy-4-carboxy-benzoyl)-tetraazacyclohexadecane
(5.) poly(2,3-dihydroxyterephthaloyl) of polyethyleneimine-Molecular Weight of polyethyleneimine about 600 (i.e. 14 nitrogens). Molecular Weight of compound about 3100.
(6.) Disodium-2,3-dihydroxyterephthalate
(7.) Sodium-2,3-dihydroxy-6-pyridine carboxylate
(8.) 2,3-Dihydroxyisophthalic acid

TABLE II

Retention of $^{238}$Pu(IV) in tissues of mice treated with various agents.[a] Results are expressed as percent of injected dose ± S.D. normalized to 100% recovery.

| | Control | CaNa₃DTPAg | 3,4,3-LICAMS | 3,4,3-LICAMC | Poly-LICAMC[f] |
|---|---|---|---|---|---|
| No. of mice | 34 | 5 | 5 | 10 | |
| Tissue | | | | | |
| Liver | 51 ± 7.0 | 17.7 ± 4.4 | 23.8 ± 7.9 | 8.7 ± 3.0 | 29.5 ± 10.7 |
| Skeleton | 31 ± 6.3 | 10 ± 1.4 | 6.6 ± 1.2 | 9.7 ± 2.0 | 10.0 ± 1.0 |
| Soft tissues | 5.1 ± 0.8 | 3.3 ± 1.4 | 1.9 ± 0.4 | 2.7 ± 0.9 | 9.1 ± 1.8 |
| GI (full) | 4.6 ± 1.1 | 5.2 | 2.5 | 8.0 | 11.5 |
| Kidneys | 2.6 ± 2.6 | 0.5 | 1.3 | 2.0 | 2.5 |
| Excreta | 6.1 ± 2.0[c] | 63.0[e] | 64.1 | 69.0[b] | 37.1[d] |

[a]Ligands (30 mole/kg) were injected (i.p.) 1 hr and mice sacrificed 24 hr after $^{238}$Pu(IV) and citrate (i.v.).
[b]For 5 mice urine, 50.2%; feces, 14.1%.
[c]Mean ± S.D. for 7 groups of mice. For 10 of those mice urine, 1.0%; feces, 1.9%
[d]Urine, 30.5%; feces 7.0%.
[e]Feces, approximately 4% (78).
[f]Poly-LICAMC has a much longer biological half-life and therefore the short time of these tests does not provide a true comparison
[g]CANa₃DIPA=C₁₄H₁₈N₁₀CaNa₄ (497.4) Diethylenetriaminepentaacetate, calcium trisodium salt While particular embodiments of the invention have been described, it will be understood, of course, that the invention is not limited thereto, since many modifications may be made; and it is therefore contemplated to cover by the appended claims any such modifications as fall within the true spirit and scope of the invention.

We claim:

1. Compound of the formula:

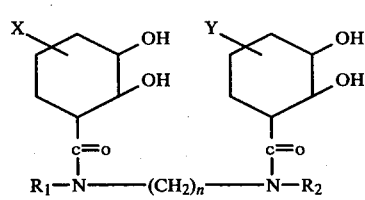

in which:
n is an integer varying from about 1-8, inclusively;
X and Y are independently selected from the group consisting of H, SO₃H, SO₃M, NO₂, and CO₂H, CO₂M;

where M represents a metal selected from the group consisting of alkali metals and alkaline earth metals, R₁ and R₂ are selected from the group consisting of alkyl and aralkyl hydrocarbon radicals and the benzamide moiety:

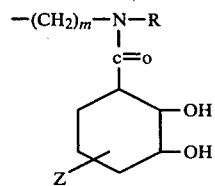

where
m is an integer varying from 1-8, inclusively and can be the same or different than n;
Z is selected from the same group as X and Y;
R is selected from the same group as R₁ and R₂.

2. A compound according to claim 1 wherein at least one of R₁ and R₂ are one or more benzamide moieties of the formula:

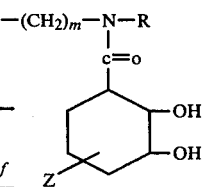

which moieties total at least three in number.

3. A compound according to claim 1 wherein the benzamide moieties present comprise a plurality of at least 5.

4. A compound according to claim 2 wherein X, Y and Z are —CO₂H.

5. A compound according to claim 2 wherein X, Y and Z are —CO₂M.

6. A compound according to claim 4 wherein the hydrocarbon radicals contain from 1-10 carbon atoms and are the same.

7. A compound according to claim 5 wherein the hydrocarbon radicals contain from 1-10 carbon atoms and are the same.

8. A compound according to claim 4 wherein the plurality of benzamide moieties is sufficient to provide a molecular weight as high as about 40,000.

9. Process for the preparation of a compound of the formula:

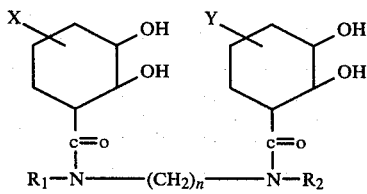

in which:

n is an integer varying from about 1-8, inclusively;

X and Y are independently selected from the group consisting of H, $SO_3H$, $SO_3M$, $NO_2$, $CO_2H$ and $CO_2M$;

where M represents a metal selected from the group consisting of alkali metals and alkaline earth metals;

$R_1$ and $R_2$ are selected from the group consisting of alkyl and aralkyl hydrocarbon radicals and the benzamide moiety:

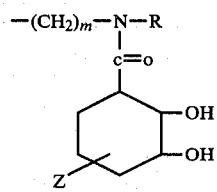

where m is an integer varying from 1-8, inclusively and can be the same or different than n;

Z is selected from the same group as X and Y;

R is selected from the same group as $R_1$ and $R_2$ with the proviso that:

said compound contains a total of at least three said benzamide moieties; which process comprises:

selective, reductive alkylation of terminal nitrogens in a polyamine corresponding to the number of nitrogens in the compound above by reacting same with an aldehyde or ketone and hydrogenating the product of the foregoing reaction;

benzamidating the polyalkylated polyamine by reacting same with a 2,3-dimethoxy or 2,3-dioxomethylene benzoyl chloride corresponding to the benzoyl, moiety in the formula above; and, demethylating the 2,3-dimethoxy benzoyl moieties of the polybenzamide so formed.

10. A process according to claim 9 where the reductive alkylation is carried out in a solvent selected from the group consisting of water, an alcohol or an aqueous solution, at a temperature of about 20°-50° C. and a pressure of about 1 to 4 atmospheres.

11. A method of selectively sequestering an actinide (IV) ion from a mammal comprising administering a chelating polybenzamide of the formula set forth in claim 1.

12. A method according to claim 11 wherein said actinide (IV) ion is Pu(IV) and said mammal is a human.

13. A method of selectively sequestering actinide (IV) ions from a liquid containing same comprising mixing a polybenzamide chelating agent as set forth in claim 1 with a fluid containing activide (IV) ions and recovering the so chelated actinide (IV) ions.

14. A process according to claim 13 wherein said actinide (IV)-ions-containing fluid is radioactive waste solution and said ions are Pu (IV).

* * * * *